(12) United States Patent
Pauly

(10) Patent No.: US 6,391,320 B1
(45) Date of Patent: May 21, 2002

(54) **COSMETIC COMPOSITION CONTAINING AN EXTRACT FROM THE SEED OF BAMBARA (*VOANDZEIA SUBTERRANEA*) NUT**

(75) Inventor: Gilles Pauly, Nancy (FR)

(73) Assignee: Laboratoires Serobiologiques (Societe Anonyme), Pulnoy (FR)

( * ) Notice: Subject to any disclaimer, the term of this patent is extended or adjusted under 35 U.S.C. 154(b) by 0 days.

(21) Appl. No.: 09/381,858

(22) PCT Filed: Feb. 17, 1998

(86) PCT No.: PCT/FR98/00306

§ 371 Date: Sep. 27, 1999

§ 102(e) Date: Sep. 27, 1999

(87) PCT Pub. No.: WO98/42305

PCT Pub. Date: Oct. 1, 1998

(30) Foreign Application Priority Data

Mar. 26, 1997 (FR) ............................................. 97 03917

(51) Int. Cl.7 ............................................... A61K 35/78
(52) U.S. Cl. .................... 424/401; 424/78.03; 424/725; 424/776; 514/937
(58) Field of Search ............................... 424/401, 195.1, 424/78.03, 725, 776; 514/937

(56) References Cited

U.S. PATENT DOCUMENTS 5,489,426 A  2/1996  Zabotto et al.

FOREIGN PATENT DOCUMENTS

| WO | 93/23069 | 11/1993 |
| WO | 94/18944 | 9/1994 |

OTHER PUBLICATIONS

Freis et al. (2000). *SOFW J.*, vol. 126, No. 4, pp. 17, 20–24 and 26–30.*

* cited by examiner

Primary Examiner—Raj Bawa
(74) *Attorney, Agent, or Firm*—Young & Thompson

(57) ABSTRACT

A cosmetic composition for topical application to the skin, the hair, the nails or the eyelashes, which contains at least one soluble protein fraction extracted from the seed of Bambara (*Voandzeia subterranea*) nut, in admixture with a cosmetologically and dermatologically acceptable excipient.

10 Claims, 3 Drawing Sheets

COSMETIC COMPOSITION CONTAINING AN EXTRACT FROM THE SEED OF BAMBARA (*VOANDZEIA SUBTERRANEA*) NUT

FIELD OF THE INVENTION

The present invention relates to the field of cosmetology and has for its object the use of extracts of Bambara (also called arachid nut or pistachio bean) nut seeds in a cosmetic product or composition, as well as a corresponding cosmetic product or composition.

BACKGROUND OF THE INVENTION

Bambara nut (*Voandzeia subterranea* (L) Thouars) is a seed of African origin used locally as a vegetable. It is an indigenous African vegetable cultivated principally by farmers as a "famine culture", one of its principal characteristics being its tolerance for drought and poor soil and its ability to grow under conditions unsuitable for arachids (peanuts).

Bambara nut seeds, which constitute a complete foodstuff, contain proteins, carbohydrates and lipids and can be consumed at different stages of maturation.

Their chemical composition (g/100 g of flour or per 100 g of dried seeds) is as follows:

proteins: 16 to 21%,
starch: 39 to 49.5%,
tannins (equivalent to tannic acid): 0.36 to 0.94%,
lipids: 5 to 7.3%,
ash: 3.65%.

It is known that the seed of *Voandzeia subterranea* contains protease inhibitors and the trypsic inhibition activity estimated by the so-called Kakade technique is according to the literature from 6.7 to 15.4 TUI/mg of flour, the functional properties of the protein isolates of said seed having been analyzed for food purposes.

SUMMARY OF THE INVENTION

However, the inventors have discovered, in a surprising manner, that the extracts of seeds of *Voandzeia subterranea* (Bambara nut), particularly the protein extracts, can be used directly in cosmetic products or compositions and permit providing specific properties and obtaining notable particular effects.

Thus, there has been noted a strong nutritive and cellular stimulant power, a softening and biofilmogenic effect, cutaneous conditioning and repair effects, anti-wrinkle effects, tightening effect, dermal protective and elastic tissue protective effects, as well as anti-irritant, anti-free radical, anti-pollution, hydrating, anti-UVB and anti-UVA photoprotection, passifying, anti-proteases, anti-elastases, anti-collagenases, anti-catalase and anti-aging and cutaneous firming effects. Bioconditioning, reparative, softening and vitalizing effects have been observed for the hair and nails after application of the mentioned extracts.

The first object of the present invention accordingly consists in the use of at least one soluble protein fraction extracted from seeds of Bambara (*Voandzeia subterranea*) nuts as an active agent in a cosmetic product or composition for the skin and/or the hair, nails and eyelashes.

The mentioned extracts can be used, not only for it skin care and hygiene applications (products for the face and body, day or night products, solar products, anti-wrinkle hygienic products, or thinning products), but also in the field of capillary care and hygiene (lotions or shampoos, creams, mousses, protective products, separators, softeners, filmogenic products and photo protectors or again products for perms and coloring).

The preparation of soluble protein extracts is carried out by conventional techniques for the extraction of vegetable proteins and for the preparation of protein concentrates or isolates, known to those skilled in the art.

BRIEF DESCRIPTION OF THE DRAWINGS

Other features and advantages of the present invention will become apparent from the following description, taken in connection with the accompanying drawings, in which:

FIG. 2=Example 2; FIG. 3=Example 3)

DETAILED DESCRIPTION OF THE INVENTION

Figure 1:
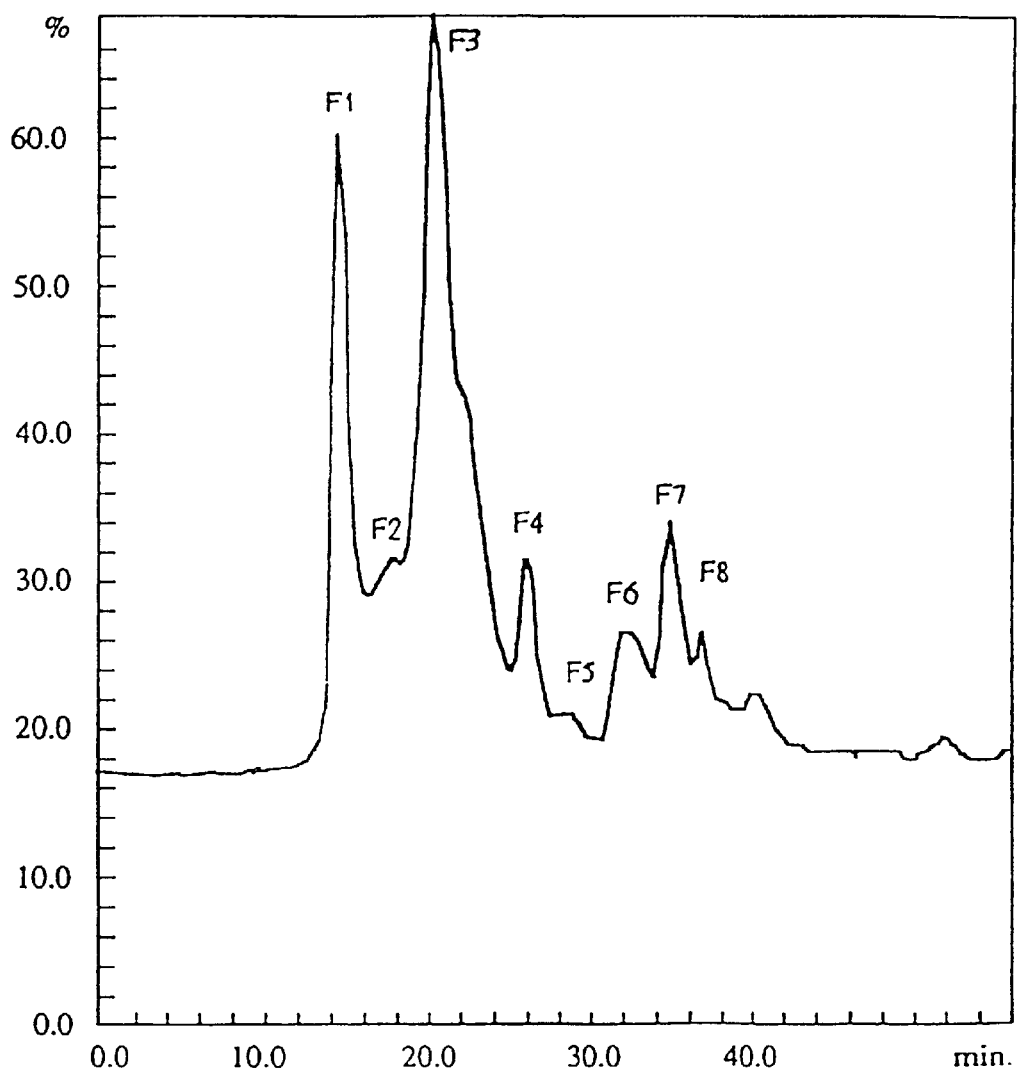
FIGS. 1 to 3 show respectively, in the form of chromatograms, the profiles of the molecular weights of the extracts obtained successively by each of the examples of the mentioned processes 1 to 3 (FIG. 1=Example 1.
Figure 2:
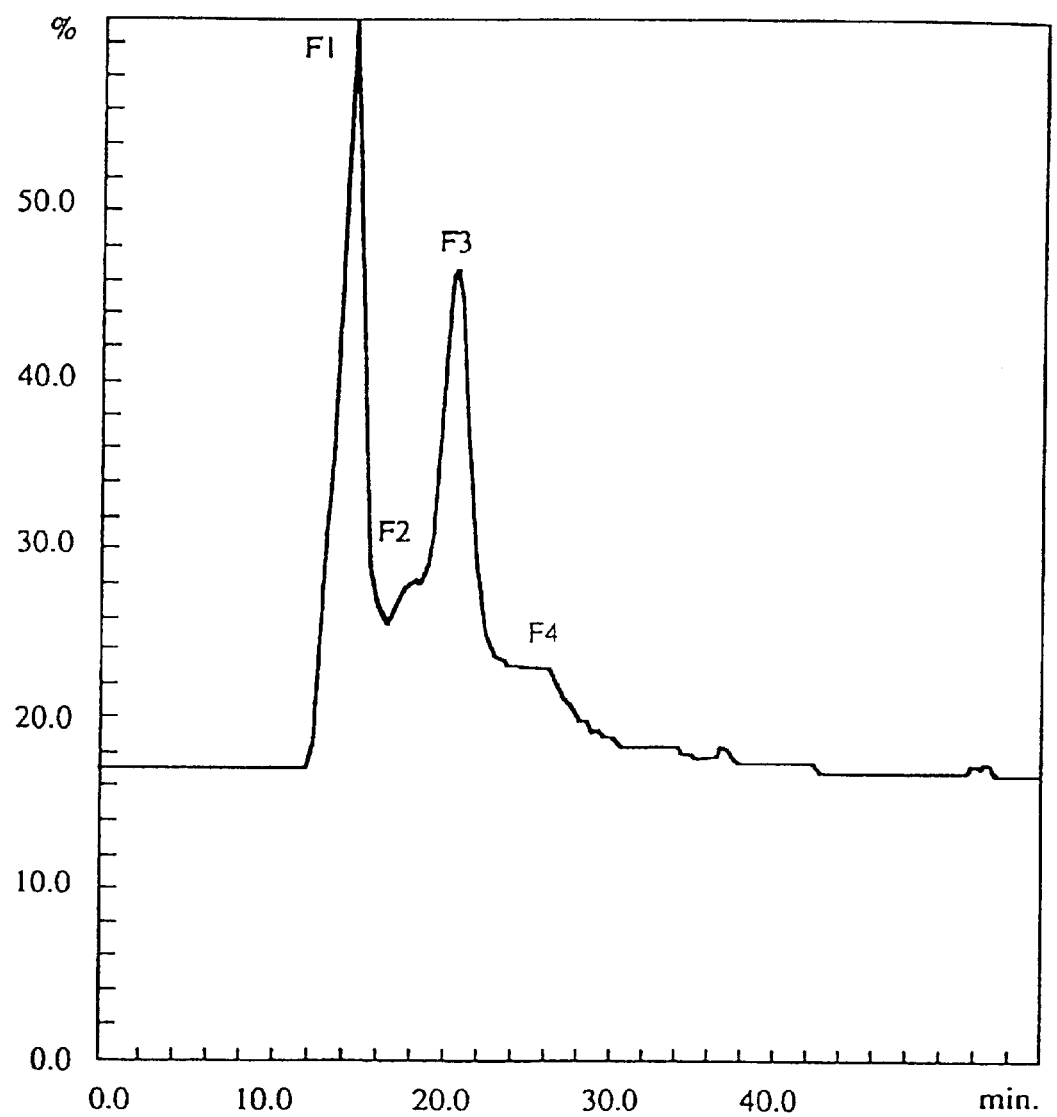
Figure 3:
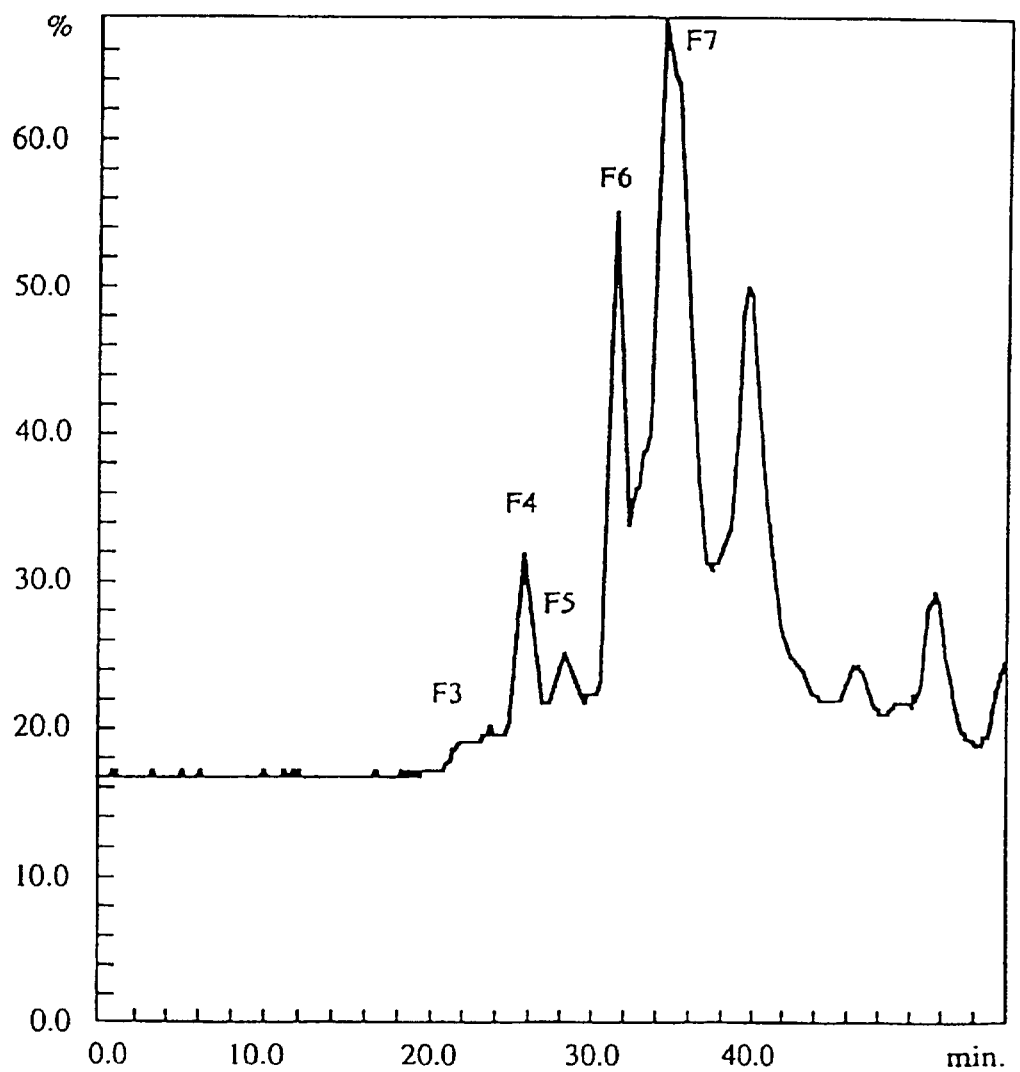

By way of non-limiting illustrative example, there will be described hereafter different processes for obtaining and preparing extracts of seeds of Bambara nuts, adapted to be used within the scope of the present invention.

EXAMPLE 1

There are added to 2.5 liters of distilled water, 250 grams of flour obtained by grinding seeds of *Voandzeia subterranea*.

After 15 minutes of agitation, the pH of the solution is adjusted to 7.5 with sodium hydroxide and the extraction is carried out for one hour at ambient temperature.

After centrifugation for 10 minutes at 5000 g, the upper lipid layer is eliminated: the tan supernatant is collected, then filtered at 0.5 $\mu$.

The solution comprises 2.5% of dry extract and has a protein concentration of 12 g/l (Biuret determination).

The extract can be dehydrated by conventional known techniques, such as spraying, lyophilization or the like.

The antitrypsic activity of the sprayed material (determined by the so-called Kakade technique) is: 33.6 TUI/mg, or an activity of the solution based on the dry extract of 840 TUI/ml.

EXAMPLE 2

There are added to 4 liters of distilled water, 400 g of flour obtained by grinding seeds of *Voandzeia subterranea*, and the solution is treated as in Example 1.

There are obtained 3.2 liters of an almost colorless solution comprising 3% dry extract and having a protein concentration of 17.8 g/l.

The pH of this solution is adjusted to 4.5 with sulfuric, hydrochloric or phosphoric acid, and then agitated for 30 minutes.

The solution is then centrifuged for 15 minutes at 5000 g and the precipitate and the supernatant are then collected.

The precipitate is placed in solution in a volume of water corresponding to 10% of the volume before precipitation and the pH of the obtained solution is adjusted with NaOH to be stable at 7.5

The solution is then again centrifuged to eliminate insolubles, and there is finally obtained a solution of 9.7% dry extract, which is dehydrated by spraying.

The antitrypsic activity of the sprayed material is 11.2 TUI/mg, or an activity of the solution based on the dry extract of 1087 TUI/ml.

EXAMPLE 3

The supernatant obtained after precipitation of the proteins according to Example 2 is filtered at 0.22µ and there is obtained a clear solution comprising 1.41% of dry extract and of a protein concentration of 1.68 g/l.

The solution is then dehydrated by spraying.

The antitrypsic activity of the sprayed material is 46.6 TUI/mg, or a theoretical activity of the solution based on the dry extract of 657 TUI/ml.

The analysis by gel permeation on a column of the superose type 12HR of the fractions extracted by the different mentioned processes, permits characterizing at least eight more or less important fractions according to the extracts.

In the drawings, there can be seen:

- a fraction (designated F1) of very high molecular weight (between 1,000,000 and 1,200,000 Da according to the standardization of the column),
- a fraction F2 of a molecular weight comprised between 400,000 and 500,000 Da,
- a fraction F3 of a molecular weight comprised between 150,000 and 180,000 Da,
- a fraction F4 of a molecular weight comprised between 30,000 and 35,000 Da,
- a fraction F5 of a molecular weight comprised between 15,000 and 18,000 Da,
- a fraction F6 of a molecular weight comprised between 4,800 and 5,500 Da,
- a fraction F7 of a molecular weight comprised between 2,100 and 2,500 Da,
- a fraction F8 of a molecular weight comprised between 1,000 and 1,300 Da.

The extracts obtained by means of the examples of processes described above are directly usable in liquid form, or after drying according to conventional dehydration techniques (spraying, lyophilization or the like).

The protein fractions can be used either in their raw form, without modification of their structures, or in the form of natural association(s) of two or all the extract fractions corresponding to the different peaks of the chromatograms shown in the accompanying drawings, or again in isolated form.

They can also be used in different galenic forms, such as solutes, liposomes, nanospheres, microspheres, microcapsules, micelles or the like.

As a modification, the protein fractions can be used in their modified form or form functionalized by means of any of the following treatments:

- polymerization,
- chemical hydrolysis of the proteins,
- enzymatic hydrolysis of the proteins by proteases of animal, vegetable, microbial or fungal origin: pepsin, trypsin, chymotrypsin, papaine, pronase, bromelain, endoprotinase, thermitase or proteases of *bacillus subtilus*, of *Aspergillus niger* and *Aspergillus oryzae* (subtilisin, alcalase, neutrase),
- microbial transformation, with the use of proteins of Bambara nut as fermentation substrate, by various microorganisms such as yeast (Saccharomyces), molds (Aspergillus) or bacteria (Bacillus and the like),
- chemical or enzymatic functionalization by processes such as desamidation, succinilation or phosphorylation,
- quaternization,
- grafting saccharide or lipid molecules.

The present invention also has for its object a cosmetic composition, particularly for topical usage for the skin and/or the hair, nails and eyelashes, characterized in that it contains at least one soluble protein fraction extracted from the seeds of Bambara (*Voandzeia subterranea*) nut.

The mentioned protein fraction(s) is or are extracted with water or an aqueous solution, particularly saline solutions with different pH, as the case may be by means of an ultrasonic generator and are purified by precipitation (modification of pH, salts, solids, temperature variation), by adsorption, by chromagraphic ion exchange or affinity or by ultrafiltration.

Preferably, said cosmetic composition contains at least one protein fraction extracted from grains of Bambara nut and enriched in protease inhibitors, the protein fraction(s) present consisting in at least one total or native protein fraction having, by gel filtration, an apparent molecular weight of 1,000,000 to 1,200,000 Da, from 400,000 to 500,000 Da, from 150,000 to 180,000 Da, from 30,000 to 35,000 Da, from 15,000 to 18,000 Da, from 4,800 to 5,500 Da, from 2,100 to 2,500 Da or from 1,000 to 1,300 Da.

The protein fraction(s) can either consist of chemical or enzymatic hydrolyzate prepared from native proteins, or be obtained by polymerization of native proteins, or else be chemically modified (quaternization, succinilation, polysaccharide or lipid grafting or the like).

According to a first modified embodiment of the invention, the cosmetic composition contains at least two soluble protein fractions extracted from seeds of Bambara nut of different apparent molecular weights.

According to a second modified embodiment of the invention, the cosmetic composition contains an extract of seeds of *Voandzeia subterranea*, constituted by all the extractable protein fractions naturally present in the seed.

Preferably, said cosmetic composition comprises between 0.01% and 50.00%, preferably between 0.50% and 15.00%, by weight of protein fraction(s) extracted from seeds of *Voandzeia subterranea*.

By way of non-limiting example of practical embodiments of the invention, there will be described hereafter different cosmetic products or compositions comprising at least one protein extract of seeds of Bambara nut.

EXAMPLE 1

A cosmetic product in the form of a protective, softening and soothing cream for the face according to the invention can for example have a weight composition constituted from the following fractions A and B, as indicated hereafter.

| Fraction A (fatty phase): | |
|---|---|
| Beeswax | 9.00% |
| Octyldodecanol | 12.00% |
| Decyl oleate | 10.00% |
| Sesame oil | 12.50% |
| Vaseline | 10.00% |
| Isopropyl myristate | 2.00% |
| Cetyl alcohol | 0.80% |
| Cholesterol | 0.30% |
| Cetyl palmitate | 2.50% |

-continued

| Fraction B (aqueous phase) | |
|---|---|
| Sorbitol | 4.00% |
| Sodium borate | 0.30% |
| Aqueous extract of Voandzeia subterranea prepared according to Example 3, (hydrosolubilized form) | 5.00% |
| Preservative LS388 (Laboratories Serabiologiques) | 2.00% |
| Water | qsp 100.00% |

The procedure for preparation and production of the above face cream consists essentially in preparing separately the fatty phase at 80° C. and the aqueous phase at 75° C. (without the extract of *Voandzeia subterranea*), then in pouring the aqueous phase into the fatty phase with turbine agitation, letting it cool and, at about 50° C., adding the extract of *Voandzeia subterranea* and finally agitating until it is cooled to ambient temperature.

EXAMPLE 2

A cosmetic product in the form of an anti-irritant, photoprotective, firming and hydrating day cream according to the invention can for example have a weight composition, constituted from the following fractions A and B, as indicated hereafter.

| Fraction A (fatty phase): | |
|---|---|
| Glycerol stearate SE | 12.00% |
| Cetyl alcohol | 1.00% |
| Hydrogenated coco glycerides | 2.00% |
| Jojoba oil | 3.00% |
| Fraction B (aqueous phase): | |
| Glycerin | 5.00% |
| Lyophilized extract of Voandzeia subterranea prepared according to Example 1 | 1.00% |
| Elestab 4112 (Laboratoires Serabiologiques) | 0.40% |
| Fragrance | 0.30% |
| Water | qsp 100.00% |

The process of preparation and production of the above day cream consists essentially in preparing separately the fatty phase at 80° C. and the aqueous phase at 80° C. (without the extract of *Voandzeia subterranea*), then pouring the fatty phase into the aqueous phase with turbine agitation, letting it cool and, at about 45° C., adding the lyophilized extract of *Voandzeia subterranea*, first dissolved in three times its weight of water, and finally continuing agitation until it cools to ambient temperature.

EXAMPLE 3

A cosmetic product in the form of a body milk with hydrating, softening, calming, anti-fatigue and elastic reinforcing properties, according to the invention could for example have a weight composition, constituted from the following fractions A and B, as indicated hereafter.

| Fraction A (fatty phase): | |
|---|---|
| Glycerol stearate (and) PEG stearate 40 | 6.00% |
| Isopropyl palmitate | 8.50% |
| Paraffin oil | 5.00% |
| Dimethicone | 0.50% |
| Cetyl alcohol | 1.00% |
| Fraction B (aqueous phase): | |
| Glycerin | 2.00% |
| Elestab 4112 (Laboratoires Serobiologiques) | 0.40% |
| Aqueous extract of Voandzeia subterranea prepared according to Example 2 (in atomized form) | 0.50% |
| Water | qsp 100.00% |

The process of preparation and production of the above body milk is substantially identical to that of the cosmetic product of Example 2

EXAMPLE 4

A cosmetic product in the form of a night cream with anti-aging, anti-wrinkle, reparative, protective and nourishing properties according to the invention can have for example a weight composition constituted from the following fractions A and B, as indicated hereafter.

| Fraction A (fatty phase) | |
|---|---|
| Glycerol stearate (and) Cetostearyl alcohol (and) Cetyl palmitate (and) Coconut glycerides | 10.00% |
| Glycerol stearate PEG 20 | 2.00% |
| Ceteareth 12 | 1.00% |
| Decyl oleate | 6.00% |
| Octyl stearate | 6.00% |
| Elestab 4121 (Laboratoires Serobiologiques) | 0.20% |
| Fraction B (aqueous phase): | |
| Glycerin | 4.00% |
| Aqueous extract of Voandzeia subterranea prepared according to Example 2 (in the form of a solute) | 10.00% |
| Elestab 305 (Laboratoires Serobiologiques) | 0.50% |
| Fragrance | 0.20% |
| Water | qsp 100.00% |

The process of preparation and production of the above night cream is substantially identical to that of the cosmetic product of Example 2.

Of course, the invention is not limited to the embodiments described and shown in the accompanying drawings. Modifications remain possible, particularly as to the constitution of the various elements or by substitution of technical equivalents, without thereby departing from the scope of protection of the invention.

What is claimed is:

1. Cosmetic composition, for topical application to at least one body region selected from the group consisting of the skin, the hair, nails and eyelashes, containing at least one soluble protein fraction extracted from the seed of Bambara (*Voandzeia subterranea*) nut, in admixture with a cosmetologically and dermatologically acceptable excipient.

2. Cosmetic composition according to claim 1, wherein the protein fraction is extracted with water or an aqueous solution.

3. Cosmetic composition according to claim 1, wherein the extracted protein fraction is purified by at least one technique selected from the group consisting of precipitation, adsorption, chromatographic ion exchange, affinity ion exchange, and ultrafiltration.

4. Cosmetic composition according to claim 1, which contains at least one protein fraction extracted from the seed of Bambara (*Voandzeia subterranea*) nut and enriched in protease inhibitors.

5. Cosmetic composition according to claim 1, wherein the protein fraction present has, by gel filtration, an apparent molecular weight selected from the group consisting of 1,000,000 to 2,000,000 Da, from 400,000 to 500,000 Da, from 150,000 to 180,000 Da, from 30,000 to 35,000 Da, from 15,000 to 18,000 Da, from 4,800 to 5,550 Da, from 2,100 to 2,500 Da, and from 1,000 to 1,300 Da.

6. Cosmetic composition according to claim 1, wherein the protein fraction consists of a chemical or enzymatic hydrolyzate prepared from native proteins.

7. Cosmetic composition according to claim 1, wherein the protein fraction is obtained by polymerization of naturally occurring proteins.

8. Cosmetic composition according to claim 1, wherein the soluble protein fraction is chemically modified by saccharide or lipid grafting.

9. Cosmetic composition according to claim 5, which contains at least two soluble protein fractions extracted from the seed of the Bambara (*Voandzeia subterranea*) nut of different apparent molecular weights.

10. Cosmetic composition according to claim 1, which contains between 0.1% and 50.00% by weight of the protein fraction extracted from the seed of Bambara (*Voandzeia subterranean*) nut.

* * * * *